Sept. 25, 1962 R. S. MOORE Plant Pat. 2,175
MINIATURE ROSE PLANT
Filed Aug. 15, 1961
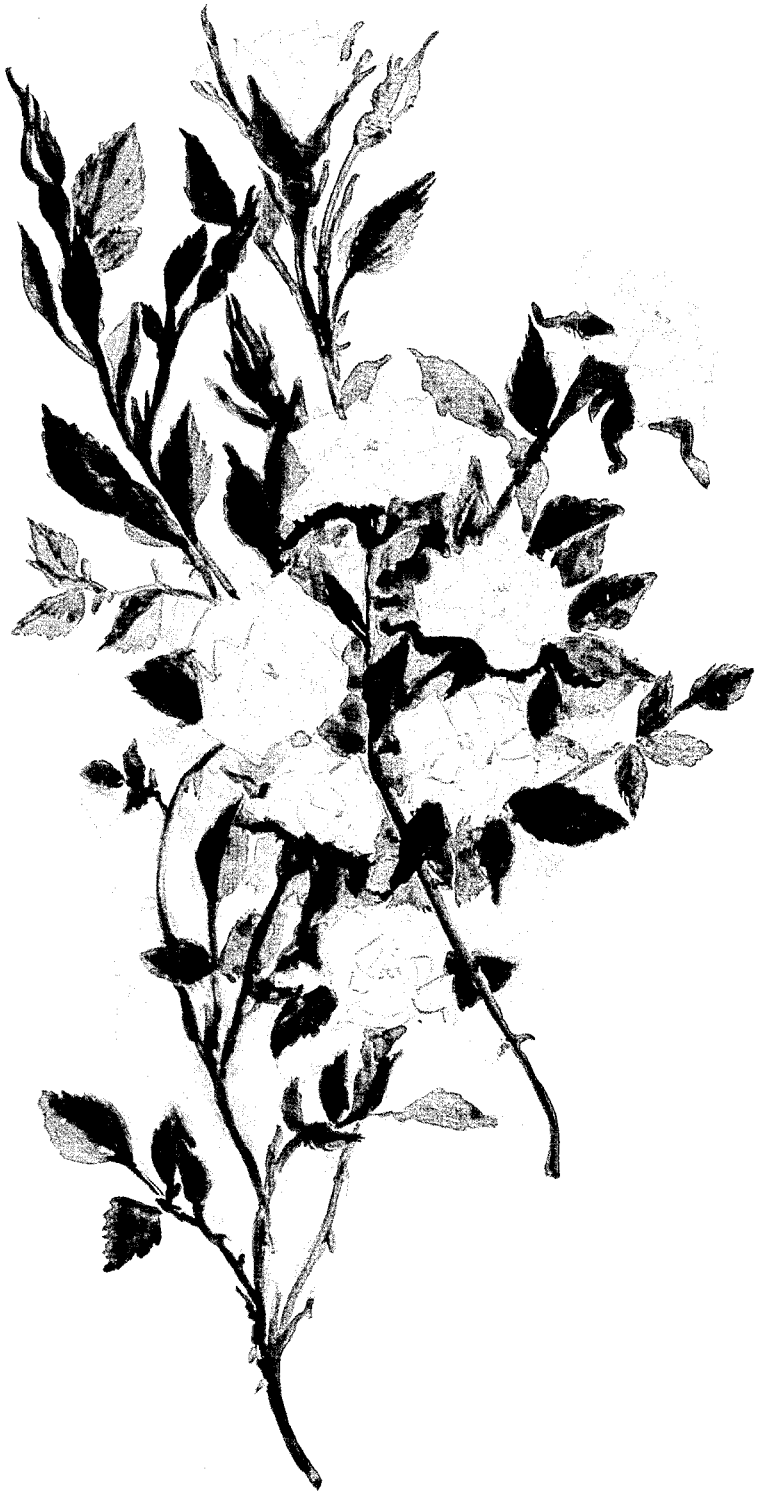
WITNESS
Jeanette Copley
INVENTOR
Ralph S. Moore
Webster & Webster
ATTYS.

United States Patent Office

Plant Pat. 2,175
Patented Sept. 25, 1962

2,175
MINIATURE ROSE PLANT

Ralph S. Moore, 2519 E. Mineral King, Visalia, Calif.

Filed Aug. 15, 1961, Ser. No. 131,694
1 Claim. (Cl. 47—61)

The present invention relates to a new and distinct variety of hybrid miniature rose plant of hardy, compact, much branched, bush type characterized, as to novelty, by the hybrid tea form of the buds and the unique color of the buds and flowers; such color being a coral pink or shrimp tone with a soft under-tone of yellow in the buds, and a tendency of the full open flowers to become more red with aging and exposure to sunlight. Additionally, the petals of the flowers are white at the base, with the white blending into the primary color of such petals.

The variety is additionally characterized, as to novelty, by soft wood cuttings which produce many slender wiry roots which contribute to ready growing in pots; a plant and flowers that grow well all season; foliage that is clean and glossy; and double-petalage flowers that keep well when cut.

As compared to the Dian miniature rose (United States Plant Patent No. 1,808), and which in general it most nearly resembles, the present variety is primarily novel and distinct in the aforementioned color of the buds and flowers.

The instant variety of miniature rose plant was originated by me in my nursery located at Visalia, California, and under conditions of careful control and observation, as a cross between two unnamed seedlings; the seed parent having been *Rosa wichuraiana* × Floradora, while the pollen parent was an unnamed seedling × Zee—all unpatented.

Subsequent to origination of the variety I successfully asexually reproduced it, in my nursery located as aforesaid, by budding as well as cuttings; the reproductions having run true in all respects.

The FIGURE of the drawings illustrates a spray, including foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; bush; seedlings; outdoors; garden decoration; cut flowers; potted plants.
Class: Hybrid miniature.

*Flowers*

Continuity: Continuous.
Fragrance: Slight.
Flowers borne: Several to stem in irregular cluster on strong, medium length stems.
Quantity of bloom: Free, outdoors.
Bud:
*Peduncle.*—Medium length; medium strength; erect—stiff; reddish-green; few to numerous red brown hairs and prickles.
*Before calyx breaks.*—Size—small. Form—long; pointed; with foliaceous appendages on the surface of the bud; with foliaceous parts extending beyond the tip of the bud equal to one-half of its length. Color—dark green, tinted reddish.
*As calyx breaks.*—Color—pink.
*As first petal opens.*—Size—small. Form—ovoid. Color—outside—Geranium Lake, 20/2; Inside—Scarlet, 19/2. Opening—opens well.

Bloom:
*Size when fully open.*—Very small, averaging 1" to 1¼".
*Petalage.*—Double, with from 20 to 30 petals arranged irregularly.
*Form.*—Full, high center at first. Petals remaining at first loosely rolled outward, becoming later at maturity very loosely rolled outward.
Petals: Thick, with both inside and outside satiny.
*Shape.*—Outside—obovate. Intermediate—obovate or lanceolate. Inside—lanceolate.
*Color.*—The general color effect is coral pink or shrimp, which tends to become more red with aging and exposure to sunlight; the petals of the flowers being white at the base with the white blending into the primary color of such petals. The specific color definitions are more particularly as follows: Newly opened flower from plant grown outdoors (July 1961)—Outside petal: outside surface—Geranium Lake, 20/3; inside surface—Scarlet, between 19/2 and 19/3. Intermediate petal: outside surface—Geranium Lake, 20/3; inside surface—Scarlet, between 19/2 and 19/3. Inner petal: outside surface—Geranium Lake, 20/2; inside surface—Scarlet, 19/2. A flower that was open for three days outdoors (July 1961)—Outside petal: outside surface—Carmen, 21/2; inside surface—Scarlet, 19/2. Inner petal: outside surface—Geranium Lake, between 20/2 and 20/3; inside surface—Scarlet, 19/2.
*Behavior.*—Drop off cleanly.
*Flower longevity (June 1961).*—Bush in garden—four to five days. Cut flowers grown outdoors, kept at living room temperatures—three to four days.

*Reproductive Organs*

Stamens: Few; arranged irregularly about pistils; mixed with petaloids.
Filaments: Short; white; most with anthers; near white.
Anthers: Small, light yellow.
Pollen: Sparse; lemon.
Pistils: Few to medium.
Styles: Uneven; medium length; medium strength; bunched.
Stigma: White or pale green.
Ovaries: All enclosed in calyx.
Hips: Ovoid; reddish; smooth; walls thin. Very few, only an occasional one will set.
Sepals: Permanent; long; spear shaped; recurved.
Seeds: Very few.

*Plant*

Foliage:
*Leaves.*—Compound of three leaflets; normal abundance; small; leathery; glossy.
*Leaflets.*—Shape—oval. Apex—acute. Base—round. Margin—serrate. Color: Mature—upper surface—dark green; under surface—normal green. Young—upper surface—normal to dark green; under surface—normal green, tinted bronze or reddish. Rachis—medium strength; upper side—grooved; under side—sparsely prickly, thorny. Stipules—medium length; medium width; with short points turning out at an angle of more than 45 degrees.
Growth:
*Habit.*—Dwarf; bushy; upright; much branched.
*Growth.*—Free.
*Canes.*—Medium strength.
*Main stems.*—Color—green. Thorns—few to several; short to medium length; hooked downward. Prickles—few. Hairs—none.

*Branches.*—Color—green. Thorns—few to several; medium length; short, moderately broad, oval shaped base. Prickles—none. Hairs—none.

*New shoots.*—Color—green-bronze. Thorns—few; hooked downward, with short oval base. Prickles—none. Hairs—none.

The miniature rose plant and its flowers as herein described may vary in slight detail due to climatic and soil conditions under which the variety may be grown; the present description being of the variety as grown at Visalia, California.

The following is claimed:

A new and distinct variety of rose plant of the hybrid miniature class and hardy, compact, much branched, bush type, as illustrated and described, characterized by the hybrid tea form of its buds and the coral pink or shrimp color of the buds and flowers, the buds having a soft under-tone of yellow, and the flowers when full open tending to become more red with aging and exposure to sunlight; the petals of the flowers being white at the base with the white blending into the color of such petals.

No references cited.